(12) United States Patent
Elliott et al.

(10) Patent No.: US 7,883,664 B2
(45) Date of Patent: Feb. 8, 2011

(54) MICROWAVE DRYING PROCESS FOR VITRIFICATION OF BIOLOGICS

(75) Inventors: Gloria Elliott, Midland, NC (US); Nilay Chakraborty, Charlotte, NC (US)

(73) Assignee: University of North Carolina at Charlotte, Charlotte, NC (US)

( * ) Notice: Subject to any disclaimer, the term of this patent is extended or adjusted under 35 U.S.C. 154(b) by 470 days.

(21) Appl. No.: 11/769,249

(22) Filed: Jun. 27, 2007

(65) Prior Publication Data

US 2009/0004048 A1 Jan. 1, 2009

(51) Int. Cl.
*A61L 2/00* (2006.01)
*H05B 6/64* (2006.01)
*H05B 6/80* (2006.01)

(52) U.S. Cl. .......................... 422/21; 219/678; 219/687
(58) Field of Classification Search .................. 422/21; 219/687

See application file for complete search history.

(56) References Cited

U.S. PATENT DOCUMENTS 4,865,871 A * 9/1989 Livesey et al. ............... 435/1.3
6,808,651 B1 10/2004 Katagiri et al.

OTHER PUBLICATIONS

Wusteman, et al. "Vitrification of large tissues with dielectric warming: biological problems and some approaches to their solution", Cryobiology 48 (2004) 179-189.*
Shalaev, E.Y. and Steponkus, P. L. "Depression of the Glass Transition Temperature of Sucrose Confined in a Phospholipid Mesophase", Langmuir 17 (2001) 5137-5140.*
Jeong-Ah Seo, et al, "Making Monosaccharide and Disaccharide Sugar Glasses by Using Microwave Oven," Journal of Non-Crystalline Solids, Elsevier B.V., p. 111-114, (2004).

* cited by examiner

*Primary Examiner*—Elizabeth L McKane
*Assistant Examiner*—Regina Yoo
(74) *Attorney, Agent, or Firm*—Hammer & Associates, P.C.

(57) ABSTRACT

The present invention relates to a biological composition which is storable above cryogenic temperature which is comprised of a vitrification solution in a glassy state. The vitrification solution is comprised of a biological material and a vitrification agent.

10 Claims, 7 Drawing Sheets

Viability response of trehalose- treated J774 cells that were microwave-processed using alternating 30 second heating and rest periods, shown as a function of final moisture content. The inset shows the total number of detached cells as a function of moisture content.

Figure 1. Bulk temperature of a 20μl droplet after cumulative heating in a microwave.

Figure 2. Sample water content as a function of cumulative microwave exposure time.

Figure 3. Viability response of J774 cells that were microwave-processed using alternating 30 second heating and rest periods, shown as a function of final moisture content. The inset shows the total number of detached cells as a function of moisture content.

Figure 4. Viability response of trehalose- treated J774 cells that were microwave-processed using alternating 30 second heating and rest periods, shown as a function of final moisture content. The inset shows the total number of detached cells as a function of moisture content.

Figure 5. Comparison of adjusted resazurin response of 10000 cells after 420s of microwave treatment [gH2O/gdw = 4.34; T = 420s of microwave treatment, C = Control].

Figure 6. Bright field images of a 20µl droplet containing J774 cells dried to a final moisture content of 4.258 gH2O/gdw.

Figure 7. Fluorescence images of regions of 20μl droplet containing J774 cells dried to a final moisture content of ~4.3 gH$_2$O/gdw.

MICROWAVE DRYING PROCESS FOR VITRIFICATION OF BIOLOGICS

FIELD OF THE INVENTION

The present invention relates to a vitrified composition which preserves biological materials above cryogenic temperatures.

BACKGROUND OF THE INVENTION

The preservation and storage of biological materials (e.g., mammalian cells) at room temperature, while maintaining the viability of the biological material, is a long unrealized goal. Existing methods available for preservation and storage of biological materials include cryo-preservation and dehydration. The use of protectant substances to enhance the viability of the biological material after recovery from storage is prevalent in both cryo-preservation and dehydration.

Cryo-preservation involves cooling the biological material to temperatures which arrest the material's biochemical and chemical processes. Preservation is maintained as long as the temperature is maintained at sufficiently low values. Cryo-preservation is currently the only technique proven to preserve mammalian biological material while maintaining the material's viability. However, cryo-preservation has its drawbacks and limitations. Cryo-preservation is expensive and limits the transportation of biological materials to locations where the required temperature may be maintained.

Dehydration involves removing water (desiccation) from the biological material in order to dramatically limit or arrest the material's biochemical and chemical processes. The storage temperature of dehydrated biological material may be above cryogenic temperature or at room temperature if the degree of drying is sufficient to arrest processes at this temperature. The extent of dehydration required may be extreme. Freeze-drying is an example of the dehydration method, wherein biological material is cooled to a temperature where ice forms and then the sample is subsequently dried under vacuum.

The dehydration of biological material suffers from a major limitation in long-term storage at ambient conditions: the degradation of the biological material by cumulative chemical stresses encountered as the vitrification solution gets concentrated in the extra-cellular space. This results in irreversible cell damage before the cells and the vitrification solution can reach a suitably low moisture content to become glassy. The degradation occurs regardless of the drying mode employed (dry-box, vacuum, etc).

U.S. Pat. No. 6,808,651 discloses a method for creating a thermoplastic shaped-body by concentrating a trehalose solution. The trehalose solution is concentrated by heating it to a temperature of at least 165° C. in order to reduce the solution's water content. However, there is no mention of using trehalose to aid in the preservation of any type of biological material. Additionally, in the present invention, heating a biological composition to a temperature in excess of 50° C., let alone 165° C., will almost certainly cause irreversible damage to the biological material contained within the composition and render it non-viable.

The use of microwaves to aid in the dehydration of biological material has met with little success. Microwave processing using non-ionizing electromagnetic radiation can actively induce the evaporation of polar molecules like water from a sample of biological material. The vibration of polar molecules in a constantly changing electrical field of microwave radiation rapidly increases the temperature of the sample. The rapid increase in temperature has numerous adverse biological effects and results in a non-viable sample.

The article, *Making Monosaccharide and Disaccharide Sugar Glasses by Using Microwave Oven*, published in the Journal of Non-Crystalline Solids, Volume 333, Issue 1, 1 Jan. 2004, Pages 111-114, discloses a method for making sugar glass without caramelization of the sugar through the use of microwaves. Additionally, the article discloses the desire to use sugar glass to conduct physical aging studies and study relaxation dynamics because of the high glass transition temperature of the sugars. The article demonstrates the utility of microwave radiation as a means to quickly remove water from materials. While the article does disclose some of the protective characteristics of trehalose on proteins and biomembranes, there is no mention of using microwave radiation on a variety of vitrification agents, including trehalose, for the preservation and storage of biological materials above cryogenic temperature, while maintaining the viability of the biological material.

A technology that facilitates dry storage of biological material above cryogenic temperatures would greatly bolster efforts in cellular and tissue engineering, cell transplantation, and biosensor technology. Hence, there exists an unsatisfied need for a composition and method to preserve and store biological materials above cryogenic temperature while maintaining the material's viability.

SUMMARY OF THE INVENTION

The present invention relates to a biological composition which is storable above cryogenic temperature which is comprised of a vitrification solution in a glassy state. The vitrification solution is comprised of a biological material and a vitrification agent.

BRIEF DESCRIPTION OF THE DRAWINGS

Total viability was calculated according to Equation (1). The inset shows the total number of detached cells as a function of moisture content.

DETAILED DESCRIPTION

The present invention refers to a biological composition which may be stored above cryogenic temperature and remains viable for later reanimation. Biological composition, as used herein, refers to a mixture which may comprise a vitrification solution and various additional liquid and solid materials. The biological composition may be comprised of a vitrification solution in a glassy state. The vitrification solution may be comprised of a biological material, a vitrification agent, and various additional materials.

Additionally, a method is described by which preservation and storage may be achieved above cryogenic temperature such that the function of the biological material may be recovered. In one embodiment of the present invention, the method involves the controlled dehydration of a vitrification solution (and the cells within this solution) using microwave energy, to create a uniformly dried biological composition via a rapid and controllable process. The method uses intermittent microwave energy to cause a small amount of heating in a vitrification solution containing biological material. This heating pulse is enough to cause water loss from the vitrification solution, but not enough to allow the local temperature to rise above 50° C. in the case of biological cells and tissues, or above the temperature of thermal denaturation in the case of proteins. By intermittently heating the vitrification solution in well-timed pulses, extensive dehydration can be achieved within minutes, thereby minimizing the time the biological material (e.g., cells, proteins, etc.) are exposed to adverse chemical stresses as the vitrification solution concentrates to the point where it will become glassy at the desired temperature. Alternatively temperature overshoot can be controlled by intermittently cycling the power on and off in response to direct thermal feedback from temperature probes (ex. Thermocouples or Infrared sensors) directed at the sample.

Some lower animals and numerous plants are capable of surviving complete dehydration. This ability to survive in a dry state (anhydrobiosis) depends on several complex intracellular physiochemical and genetic mechanisms. Among these mechanisms is the intracellular accumulation of sugars (e.g., saccharides, disaccharides, oligosaccharides) which act as a protectant during desiccation. Trehalose is one example of a disaccharide naturally produced in desiccation tolerant animals.

Sugars may offer protection to desiccation tolerant animals in several different ways. A sugar molecule may effectively replace a hydrogen-bounded water molecule from the surface of a folded protein without changing its conformational geometry and folding due to the unique placement of the hydroxyl groups on a trehalose molecule. A sugar molecule may also prevent cytoplasmic leakage during rehydration by binding with the phospholipid heads of the lipid bilayer. Furthermore, many sugars have a high glass transition temperature, allowing them to form an above cryogenic temperature or a room temperature glass at low water content. The highly viscous 'glassy' state reduces the molecular mobility, which in turn prevents degradative biochemical reactions that lead to deterioration of cell function and death.

In unprotected mammalian cells, desiccation stress causes severe membrane damage and denaturation of cellular protein which results in cell death. However, through the addition and/or imbibition of vitrification agents (e.g., sugars) the survival of several desiccation intolerant biological materials may be improved during drying, including, but not limited to, human mesenchymal stem cells, murine fibroblast cells, blood platelets, bacteria, viruses, mammalian cell membranes, liposomes, and enzymes. To impart its protective effect during desiccation, the vitrification agent may be present on both sides of the cell membrane. Generally, the vitrification agent will not permeate the cell membrane without outside aid. To achieve permeation, a variety of techniques have been explored in order to find an efficient mechanism to introduce vitrification agents inside cells. These include transfection, engineered pores, microinjection, and endocytosis.

The method described above also offers an additional beneficial effect of uniformity within the biological composition. Classic ambient drying techniques (e.g., dry box, vacuum, freeze drying) lead to non-uniform samples with cells clustered in the water-rich region of the non-homogeneous vitrification solution. The intermittent microwave method described herein may also help prevent the 'skinning effect' (creation of a glassy outer layer that reduces the rate of water loss from the central portion of the sample) that accompanies many classic ambient drying methods.

Storable or storage, as used herein, refers to a biological composition's ability to be preserved and remain viable for use at a later time. Above cryogenic temperature, as used herein, refers to a temperature above −150° C. Room temperature, as used herein, refers to a temperature range between 18 and 26° C. The duration a biological material may remain viable during storage above cryogenic temperature may vary from one material to the next. In one embodiment, a biological material may remain viable while in storage above cryogenic temperature for 2-20 days. In another embodiment, a biological material may remain viable while in storage above cryogenic temperature for 10 weeks. In yet another embodiment, a biological material may remain viable while in storage above cryogenic temperature for up to one year. In yet another embodiment, a biological material may remain viable while in storage above cryogenic temperature for up to 10 years.

Vitrification, as used herein, is a process of converting a material into a glass-like amorphous material. The glass-like amorphous solid may be free of any crystalline structure. Solidification of a vitreous solid occurs at the glass transition temperature $T_g$.

Solution, as used herein, refers to either a homogenous or heterogeneous mixture of solids and liquids. A homogeneous solution is one which has a definite, true composition and properties (e.g., any amount of a given solution has the same composition and properties as any other amount of the same solution). A heterogeneous solution is one that has a definite composition, however any amount of a given solution may not have the same composition any other amount of the same solution. In one embodiment, a homogenous solution may include a biological material and a vitrification solution wherein the biological material is uniformly distributed throughout the vitrification solution. In another embodiment, a heterogeneous solution may include a biological material and a vitrification solution wherein the biological material is non-uniformly distributed throughout the vitrification solution.

Vitrification solution, as used herein, refers to a solution which is comprised of a vitrification agent and a biological material. The vitrification solution is capable of vitrifying at its glass transition temperature ($T_g$). In one embodiment, the vitrification solution may be comprised of water, a vitrification agent, and an organ to be transplanted. In another embodiment, the vitrification solution may be comprised of water, a disaccharide, and mammalian cells. In yet another embodiment, the vitrification solution may be comprised of trehalose and cellular proteins. In yet another embodiment, the temperature of the vitrification solution may not rise above 50° C. in the case of biological cells and tissues, or above the temperature of thermal denaturation in the case of proteins.

Biological material, as used herein, refers to materials which may be removed or derived from living organisms. Examples of biological materials include, but are not limited to, proteins, cells, tissues, organs, cell-based constructs, or combinations thereof. In one embodiment, biological material may refer to mammalian cells. In yet another embodiment, biological material may refer to a heart, lungs, or kidney to be used in a transplant procedure. In yet another embodiment, biological material may refer to human mesenchymal stem cells, murine fibroblast cells, blood platelets, bacteria, viruses, mammalian cell membranes, liposomes, enzymes, or combinations thereof.

Vitrification agent, as used herein, is a material that forms a glass, or that suppresses the formation of crystals in other materials, as the mixture cools or densities. The vitrification agent may also provide osmotic protection or otherwise enable cell survival during dehydration. Vitrification agents include, but are not limited to, dimethylsulfoxide, glycerol, sugars, polyalcohols, methylamines, betaines, antifreeze proteins, synthetic anti-nucleating agents, polyvinyl alcohol, cyclohexanetriols, cyclohexanediols, inorganic salts, organic salts, ionic liquids, or combinations thereof. In one embodiment, the vitrification agent may be any water soluble solution that yields a suitable glass for storage of biological materials. In another embodiment, the vitrification agent may be a disaccharide. In yet another embodiment, the vitrification agent may be trehalose. In yet another embodiment, the vitrification agent may be imbibed within a cell, tissue, or organ.

Glassy state, as used herein, refers to a state of matter. An amorphous material enters its glassy state when it passes below its glass transition temperature ($T_g$). The glassy state combines some properties of crystals and some of liquids but remains distinctly different from both. In one embodiment, glassy state may refer to the state the biological composition enters upon dropping below its glass transition temperature. In another embodiment, the glassy state may refer to the state the vitrification solution and/or vitrification agent enters upon dropping below its glass transition temperature. In yet another embodiment, the glassy state may have the mechanical rigidity of a crystal, but the random disordered arrangement of molecules that characterizes a liquid.

Water-soluble, as used herein, refers to the ability for a given substance, the solute, to dissolve in water, the solvent. In one embodiment, water-solubility may be measured in terms of the maximum amount of solute dissolved in a solvent at equilibrium. The resulting solution is called a saturated solution. In another embodiment, water-soluble may refer to the vitrification agent's ability to dissolve in water.

Amorphous material, as used herein, is a material in which there is no long-range order of the positions of the atoms. Conversely, materials in which there is long-range atomic order are called crystalline materials or morphous. Amorphous materials are often prepared by rapidly cooling molten material, such as glass. The cooling reduces the mobility of the material's molecules before they can pack into a more thermodynamically favorable crystalline state. Additives which interfere with the primary constituent's ability to crystallize may produce amorphous material. In one embodiment, the vitrification solution may be an amorphous material. In another embodiment, the vitrification agent may be an amorphous material. In yet another embodiment, the biological composition may be an amorphous material.

Glass transition temperature ($T_g$), as used herein, is the temperature above which amorphous materials (e.g., a vitrification solution) behave like liquids and below which amorphous materials behave in a manner similar to those of a crystalline phase and enters the glassy state. This is not a fixed point in temperature, but is instead variable dependent on the timescale of the measurement used. In one embodiment, the vitrification solution may have a glass transition temperature in the range of −150° C. to 30° C.

Microwaves, as used herein, refers to electromagnetic waves having operating frequencies anywhere from 0.3 GHz to 300 GHz. Microwaves are commonly used in the food, communication, and chemical industries. Microwaving, as used herein, refers to the use of non-ionizing electromagnetic radiation to actively induce the evaporation of polar molecules (e.g., water) from a biological composition. The vibration of polar molecules in a constantly changing electrical field of microwave radiation increases the temperature of the system quickly. Increase of temperature is perhaps the most important factor associated with microwave radiation and the majority of the effects on biological materials are directly related to the heating effect. The maximum output power of the microwave may vary in the range of 1 Watt (W) to 600 W. In one embodiment, the microwave maximum output power may be 600 W. In another embodiment, the microwave maximum output power may be 300 W. In yet another embodiment, the microwave maximum output power may be 100 W. In yet another embodiment, the microwave maximum output power may be 1 W.

Biological materials may endure severe damage at multiple levels resulting from exposure to high levels of microwave radiation. Damage may include, but is not limited to, cell membrane degradation, cellular protein denaturation, damage to the sub-cellular components, or combinations thereof. The increase in temperature limits the time the biological material may be continuously exposed to microwave radiation. The duration of microwave exposure is directly related to the heat generated by the microwave radiation in the biological material. The intermittent supply of drying energy may be used to control and regulate the temperature of biological materials exposed to microwave radiation. In one embodiment, the energy can be delivered according to the drying kinetics of the specimen itself.

First period of time, as used herein, refers to a preset period of time. Second period of time, as used herein, refers to a preset period of time. In one embodiment, the first period of time may refer to a period wherein a vitrification solution may be exposed to microwave radiation and the second period of time may refer to a period wherein a vitrification solution is allowed to rest. In another embodiment, the first period of time may refer to a period wherein a vitrification solution may be allowed to rest and the second period of time may refer to a period wherein a vitrification solution may be exposed to microwave radiation. In yet another embodiment, the first period of time may refer to a 1-120 second period wherein a vitrification solution may be exposed to microwave radiation and the second period of time may refer to a 1-120 second period wherein a vitrification solution is allowed to rest.

Desiccation energy, as used herein, refers to the energy required to dry out a material and/or solution to a desired level of moisture. In one embodiment, desiccation energy may refer to energy from a radiant heat source. In another embodiment, desiccation energy may refer to energy supplied to a dry box. In yet another embodiment, desiccation energy may refer to energy supplied by a vacuum chamber.

EXAMPLE SUMMARY

Cell Culture: J774.A1 mouse macrophage cells were obtained from American Type Culture Collection (Manassas, Va.). Cultures were maintained at 37° C., 10% $CO_2$-90% air in cell culture media consisting of Dulbecco's Modified Eagle Medium (DMEM) with 4.5 g/L glucose (Mediatech Inc, Herndon, Va.), 10% fetal bovine serum (FBS; Mediatech Inc, Herndon, Va.) and 1% 5000 I.U. Penicillin, and 5000 µg/ml Streptomycin solution (Mediatech Inc, Herndon, Va.). Cells were first cultured in 25 $cm^2$ cell culture T-flasks (Corning Incorporated, N.Y.) for 3 days. As cells neared confluence they were detached from flasks by scraping and then transferred into 50 ml spinner culture flasks (Wheaton Millville, N.J.). All cells used for experiments were taken from established spinner flask cultures that were maintained at a density of less than $1 \times 10^6$ cells/ml.

Trehalose Loading and Detection: Macrophage cells have the capacity to take up solutes from the extracellular milieu by fluid phase endocytosis. This approach was used to deliver trehalose into the intracellular space. Cells were suspended in regular culture media that was supplemented with 50 mM trehalose and then incubated for 18 hours in 50 ml spinner culture flasks (Wheaton Millville, N.J.). Following incubation for the pre-determined time period, an aliquot of cell suspension was removed and the cells were collected by centrifugation, washed three times in PBS, and then lysed by freeze-thaw in ultra high purity 18 mOhm water. The lysed solution was centrifuged and the supernatant collected and prepared for high performance liquid chromatography analysis. An eighteen inch Dionex Carbo PAC HPLC column (Dionex Sunnyvale, Calif.) and ESA Coulochem II electrochemical detector (ESA Chelmsford, Mass.) were used for sugar determination.

Microwave Drying Protocol: High purity, low endotoxin trehalose dihydrate was obtained from Ferro Pfanstiehl (Waukegan, Ill.). Isotonic trehalose solution was prepared by adding 1 part 1×PBS solution (Mediatech Inc, Herndon, Va.) to 2 parts of 300 mM Trehalose solution prepared in distilled water. This yielded a 200 mM trehalose solution with an average osmolality of 308 mOsm. The osmolality of solutions was measured using a micro-osmometer (Fiske Associates, Norwood, Mass.).

An aliquot of 5 ml of cell suspension was collected from spinner flask culture and centrifuged at 175×g for 5 min using a Centra CL2 Centrifuge (Thermo Electron Corp., FL). The supernatant was decanted and the cell pellet was resuspended in 1.0 ml of fully complemented Dulbecco's Modified Eagle medium for cell counting in a hemacytometer (Hausser Scientific, Horsham, Pa.), using 0.4% Trypan Blue (Sigma-Aldrich, Mo.) exclusion as an indicator of membrane integrity and viability. Based on this count a cell concentration of $5 \times 10^5$ viable cells/ml in full complement media was prepared. Cells were plated onto 22 mm square plastic cover slips (Fisher Scientific, Pittsburgh, Pa.) in 20 µl droplets (~10,000 cells/droplet). The cover slips was placed in 35 mm×10 mm tissue culture treated cell culture dishes (Corning Incorporated, N.Y.) and placed inside the incubator for 45 min to allow the cells to attach to the surface of the coverslip. Following the incubation period the media was carefully removed by pipette and an equal volume of 200 mM trehalose-PBS drying solution was placed on top of the plated cells. This sample was then placed in a single phase 120 volt 2450 MHz Microwave oven (Danby, Ontario, Canada; input specification: 60 Hz AC, 1.05 KW, grounded). This unit has a maximum output power of 600 W.

To avoid over-heating the samples, several heating processes were evaluated. Samples were heated in steps, alternating between active heating steps at full power, and passive cooling steps, wherein the sample was allowed to rest inside the microwave cavity with the door open. This process facilitated acquisition of temperature data between heating periods. Active heating periods between 15 and 45 seconds were evaluated. The passive cooling step was held constant at 30 s. Immediately after the power was terminated in each heating step, the microwave door was opened, a K type thermocouple was embedded into the central region of the droplet, (Omega Engineering Inc., Stamford, Conn.) and the temperature was recorded on a single input printing thermometer (Model 08533-41, Cole Parmer, Vernon Hills, Ill.). Samples were heated until the sample appeared glassy or solid-like to the eye.

Using the optimized heating profile, mass loss curves as a function of cumulative microwave heating time were generated. The initial and final weights were determined and used to calculate moisture contents (grams of water per gram of dry weight). The dry weight of the sample was found by preparing parallel samples in the same manner and drying them at 110° C. for 24 hours in a vacuum oven, in replicates of 6.

The viability of microwave-processed cells was evaluated as a function of final moisture content. Immediately after microwave processing the coverslip was removed from the microwave and placed into a P-35 cell culture dish. It was then rehydrated with 100 µl of fully complemented Dulbecco's Modified Eagle medium that had been pre-warmed to 37° C. Samples were then placed in the incubator for 45 minutes to provide time for reattachment to the surface of the coverslip prior to viability assessment.

Viability Assessment: Cell viability was determined using Trypan Blue and Calcein-AM/Propidium Iodide membrane integrity assays (Molecular Probes, Eugene, Oreg.). The stock solution for the Calcein-AM/Propidium Iodide staining was prepared by adding 10 µl of 1 mg/ml Calcein AM solution (aq.) and 5 µl of 1.0 mg/ml solution Propidium Iodide solution (aq.) to 10 ml of Phosphate-buffered Saline (Mediatech Inc, Herndon, Va.). Following the recovery period in the incubator, the entire 100 µl droplet was gently removed (leaving behind the cells which were attached to the coverslip surface) and collected into a 0.5 ml eppendorf tube. The viability of detached cells in this aliquot was determined by staining with 0.4% Trypan Blue solution and counting in a hemacytometer (Hausser Scientific, Horsham, Pa.). An aliquot of 120 µl of Calcein-AM/Propidium Iodide solution in PBS was added to the attached cells on the coverslip and the sample was then incubated at 37° C. for 5 min. These samples were then imaged using an inverted research microscope (Olympus Biosystems 1×81; Olympus America Inc., Melville, N.Y.) with FITC and PI fluorocubes. The attached cell viability was determined by counting the live (green) and dead (red) cells on three representative images from the same sample. The total viability was estimated by the following formula which takes into consideration the viability of both detached and attached cells:

$$\text{Total Viability} = \frac{\text{Number of viable detached cells}}{10,000} + \frac{10,000 - \text{Total of detached cells}}{10000}\left(\begin{array}{c}\text{Fractional}\\ \text{Viability of}\\ \text{attached cells}\end{array}\right)$$

Long term viability of the microwave processed cells was determined using a metabolic assay based on the reduction of resazurin. The blue and non-fluorescent dye resazurin is reduced to pink and highly fluorescent resorufin by the metabolic activity of living cells. Resazurin was obtained in powdered form (Sigma Aldrich Co., Milwaukee, Wash.). A stock solution of 110 g/ml was prepared in phosphate-buffered saline (Mediatech Inc, Herndon, Va.), sterile-filtered, and then stored in the dark at 4° C. Microwave processed cell specimens on coverslips were placed inside the wells of a 24-well plate (Corning Incorporated, N.Y.), rehydrated with fully complemented media, and then placed inside the incubator at 37° C. Metabolic function assessment was performed after 4-, 8-, 18.75-, 24-, 30-, 42-, 48-, and 54.5-hour recovery periods. One hour prior to the assay point cell cultures were removed from the incubator, the media removed, and 500 mL of phenol red-free fully complemented medium with 10% resazurin solution was added to each well. Following the addition, the plates were incubated for 60 minutes at 37° C. in the dark. After incubation, the cell viability was assessed in terms of Arbitrary Fluorescence Units (AFU) using a fluorescent plate reader (Synergy HT, Bio-Tek Instruments, Vt.) with a 530 nm excitation and a 590 nm emission filter set. Following each measurement, the resazurin solution was removed from the wells, replaced with 500 ml of full-complement culture medium, and the plates were returned to the incubator.

The distribution of the cells within the dried droplets were determined using both brightfield and fluorescence microscopy. Calcein-AM and Propidium Iodide stains were used for fluorescence live-dead staining of the cells as described previously and images were acquired in various regions that spanned the droplet. For comparison purposes equivalent samples were also dried to the same moisture content using a conventional desiccation chamber and imaged in the same manner. Macroscopic differences in the distribution of solids were noted by eye, and representative brightfield images were obtained to demonstrate the differences in drying characteristics by the two different techniques.

Results

Process Optimization: Cells that were incubated in trehalose solution for 18 hours were determined to have loaded 160 mM±50 mM trehalose during this time, a portion of which would be expected to be distributed in the cytoplasm, and the remainder residing in the endosomes.

Figure 1:
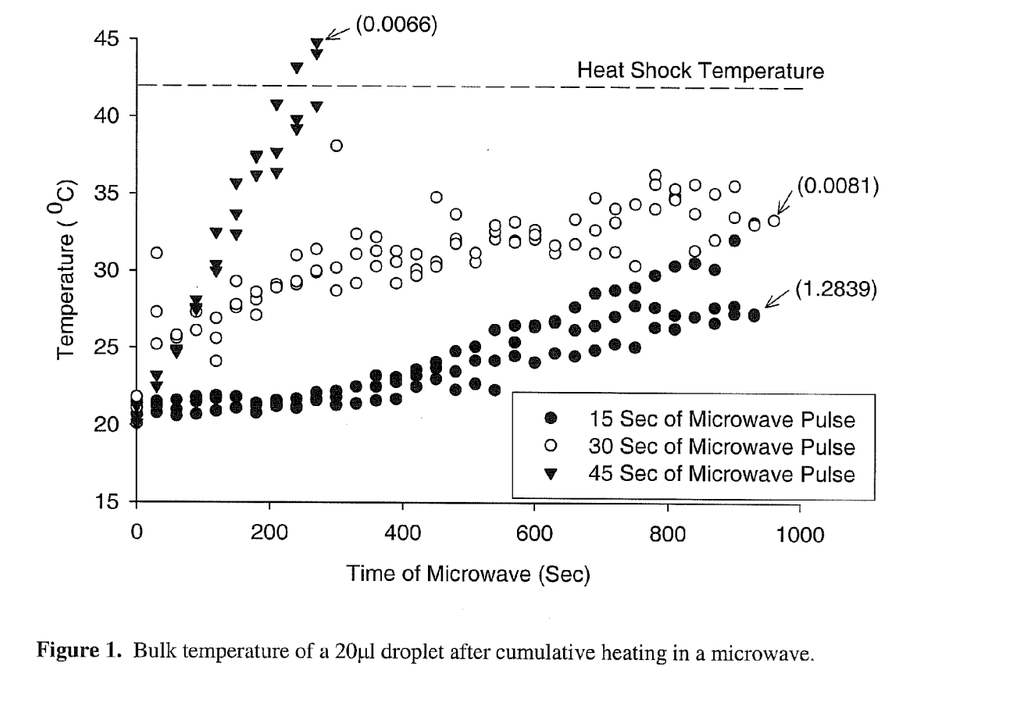
FIG. 1. Bulk temperature of a 20 microliter (µl) droplet after cumulative heating in a microwave. The inset legend indicates the duration of the active heating period. In all cases samples were allowed to cool for 30 seconds (s) between heating periods. This cooling period is not included in the total time, hence the abscissa reflects cumulative heating time, not cumulative process time. The level of dryness achieved by the end of the process is shown in brackets, expressed in units of $gH_2O/gdw$.

In FIG. 1 the temperature at the interior of the droplet was plotted as a function of cumulative microwave heating time for several different active heating periods. As expected, the extent of heating was found to be directly proportional to the length of microwave processing at full power (600 Watts). The level of dryness that was achieved by the end of the process is shown in the brackets, expressed in units of $gH_2O/gdw$. Because of the dipole heating action of the microwave energy the temperature of the samples can increase quickly, thus moderate active heating periods are necessary to avoid large thermal excursions. Because of the nature of the temperature measurement procedure, some delay (seconds) in acquiring the temperature is unavoidable. As such, the recorded temperature represents a low estimate of the true temperature. Furthermore the temperature also represents an average value for the interior portion of the droplet, and the spatial positioning can be considered accurate to only a few millimeters. The utility in this measurement is in the delineation of a reasonable heating profile that avoids a persistent excursion above 50° C. Above this temperature the induction of a heat shock response is likely in the cells. An active heating period of 15 or 30 seconds did not result in a recorded temperature above typical physiological temperatures, whereas significant heating was observed for 45 second active heating periods.

Figure 2:
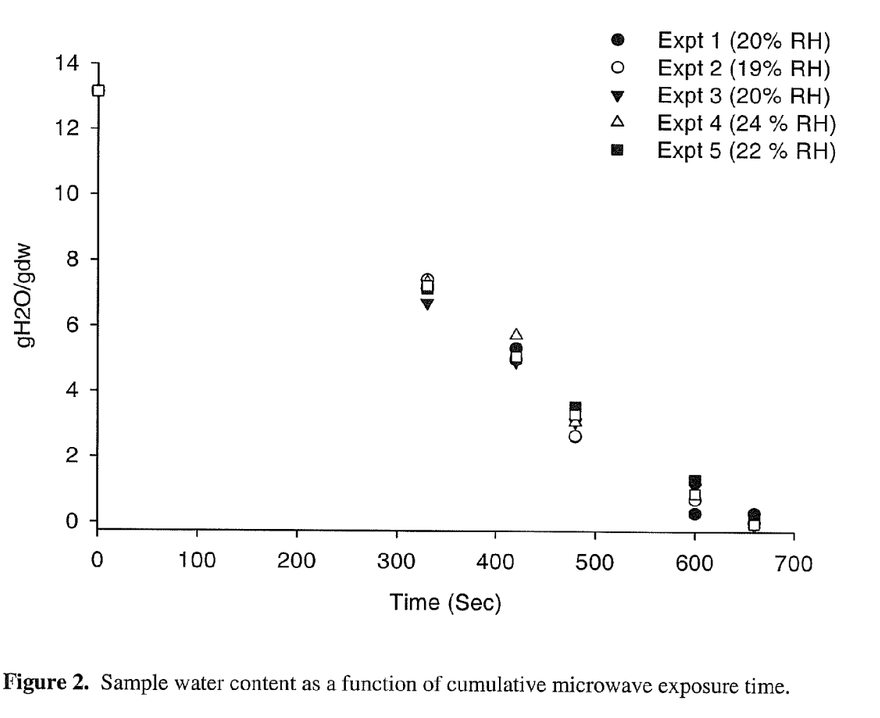
FIG. 2. Sample water content as a function of cumulative microwave exposure time. The microwave was activated for a period of 30 seconds out of every minute. The ambient relative humidity during the experiment was recorded using a sling psychrometer.

Drying Characteristics: Microwave treatment of the cell samples resulted in a systematic water loss from the sample as shown in FIG. 2. The weight loss data is represented in grams of water per gram of dry weight of the samples and the weight measurements were obtained using a high precision analytical balance (Mettler Toledo AX Series Analytical Balance, Columbus, Ohio). The drying rate was observed to be influenced by the local relative humidity; hence values of relative humidity are included with each data set.

Figure 3:
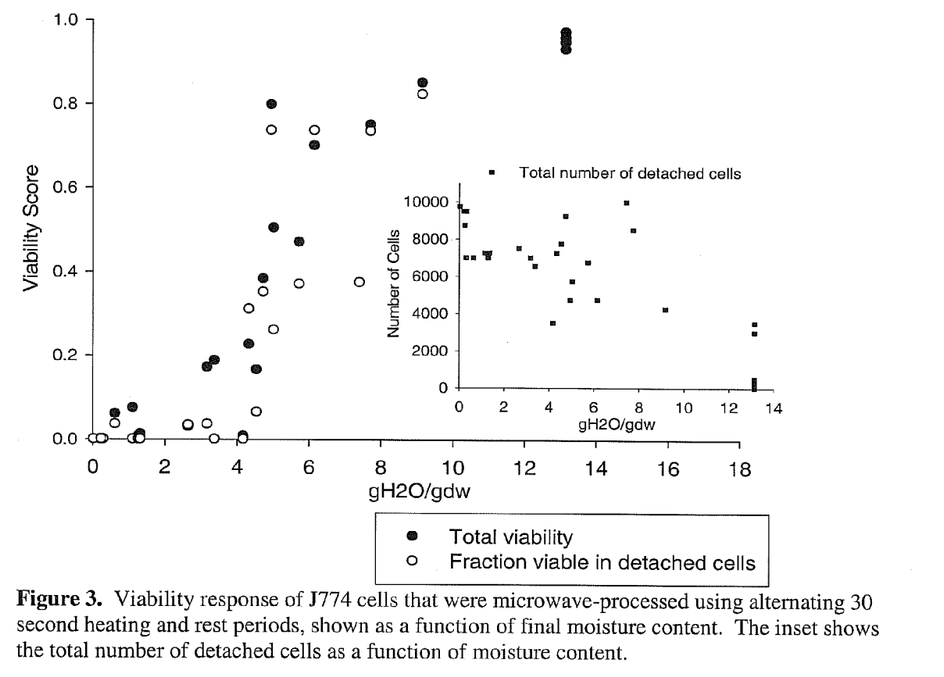
FIG. 3. Viability response of J774 cells that were microwave-processed using alternating 30 second heating and rest periods, shown as a function of final moisture content. The viability of detached cells was determined using Trypan Exclusion. The viability of attached cells was determined using Calcein-AM and Propidium Iodide staining. Total viability was calculated according to Equation (1). The inset shows the total number of detached cells as a function of moisture content.
Figure 4:
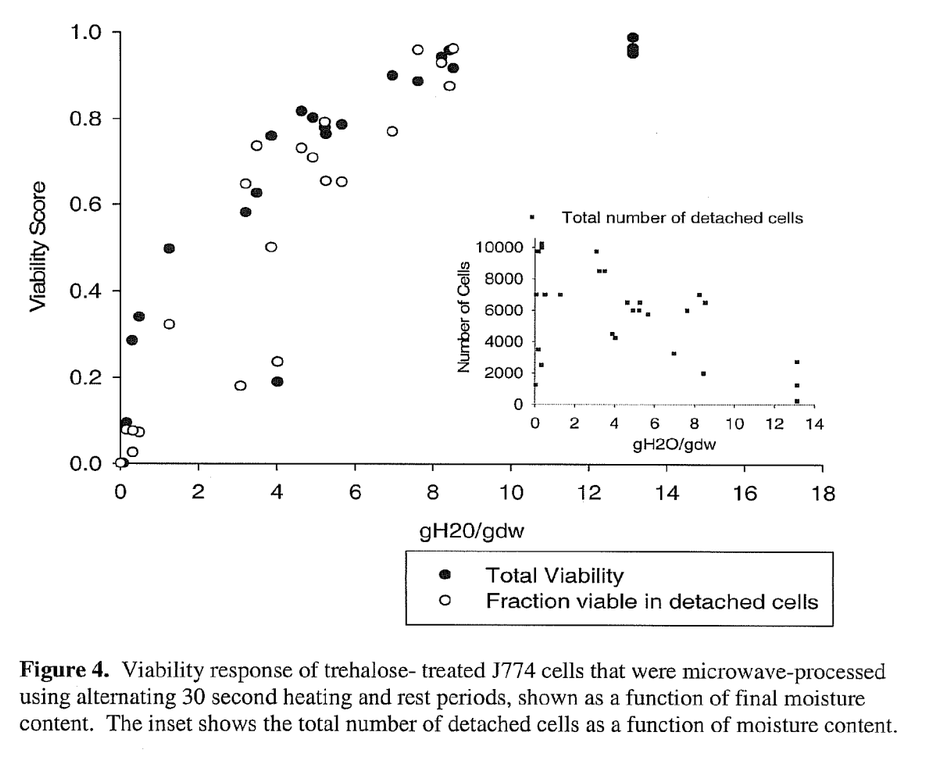
FIG. 4: Viability response of trehalose-treated J774 cells that were microwave-processed using alternating 30 second heating and rest periods, shown as a function of final moisture content. The viability of detached cells was determined using Trypan Exclusion. The viability of attached cells was determined using Calcein-AM and Propidium Iodide staining.

The characteristic cell survival 45 minutes after microwave exposure was determined using standard viability assays. Membrane integrity was determined using Trypan Blue staining on detached cells and Calcein-AM and Propidium Iodide staining for attached cells. The graph in FIG. 3 shows the total viability (calculated using equation 1) of the microwave treated cells that do not have exogenous intracellular protection. The viability of the detached fraction of cells is also shown. Both of these data sets follow a similar trend. The inset graph also shows the total number of detached cells at different levels of dryness during the microwave drying process. As the sample gets progressively drier, the number of cells that remain attached to the surface upon rehydration decreases. At the lowest moisture levels almost all of the plated cells are detached upon rehydration. The graph in FIG. 4 displays similar viability data for cells that had been previously incubated with intracellular trehalose prior to the microwave drying process. As expected, cells that accumulated intracellular trehalose demonstrated a greater tolerance of moisture loss than the control cells. This trend is consistent with other drying modalities and demonstrates the osmotic protection provided by trehalose. The inset graph also demonstrates a similar relationship with moisture content as the control cells, with the number of detached cells upon rehydration increasing as the drying progresses, with the exception that more variability in the data is observed at low moisture contents.

Figure 5:
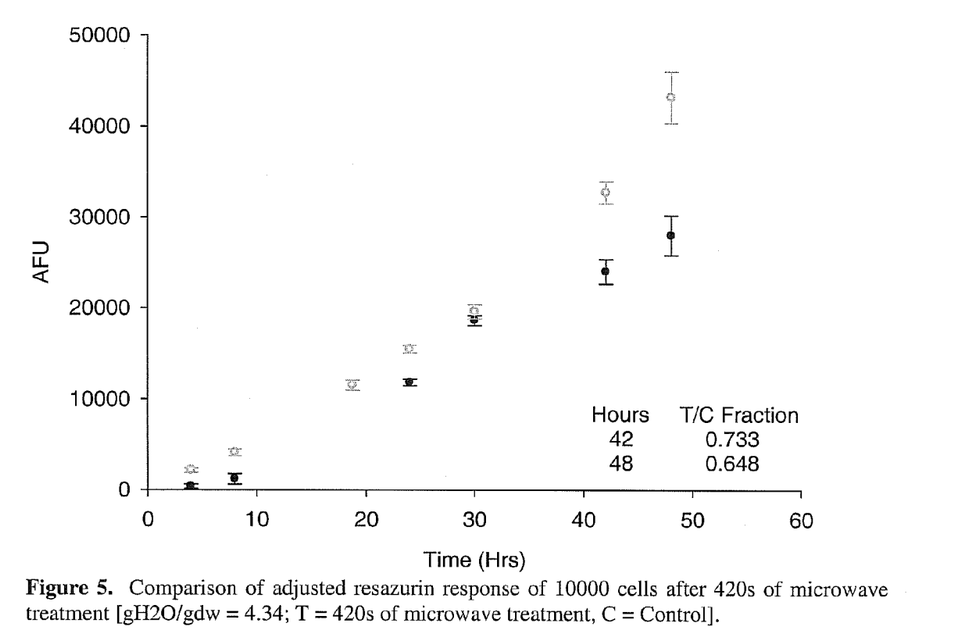
FIG. 5: Comparison of adjusted resazurin response of 10000 cells after 420 s of microwave treatment [gH2O/gdw=4.34; T=420 s of microwave treatment, C=Control]. Cells had been exposed to 50 milliMolar (mM) trehalose for 18 hours prior to processing. n=5.

In FIG. 5 the fluorescence emission of resazurin is shown as a function of cell culture time. The metabolism of resazurin is indicative of the total number of metabolically active cells and hence increasing fluorescence over time generally demonstrates growth of cells. Cell samples that had been previously incubated in trehalose for 18 hours were microwaved for an accumulative time of 420 s (30 s active/30 s rest) as described previously. An initial concentration of 10,000 cells per droplet was used. After 48 hours the fluorescence signal in microwave processed cells was 64.8% of the signal in control cells. This fraction was consistent with the number of living cells in the sample 45 minutes after the treatment, as assessed by Calcein-AM/propidium iodide staining.

Figure 6:
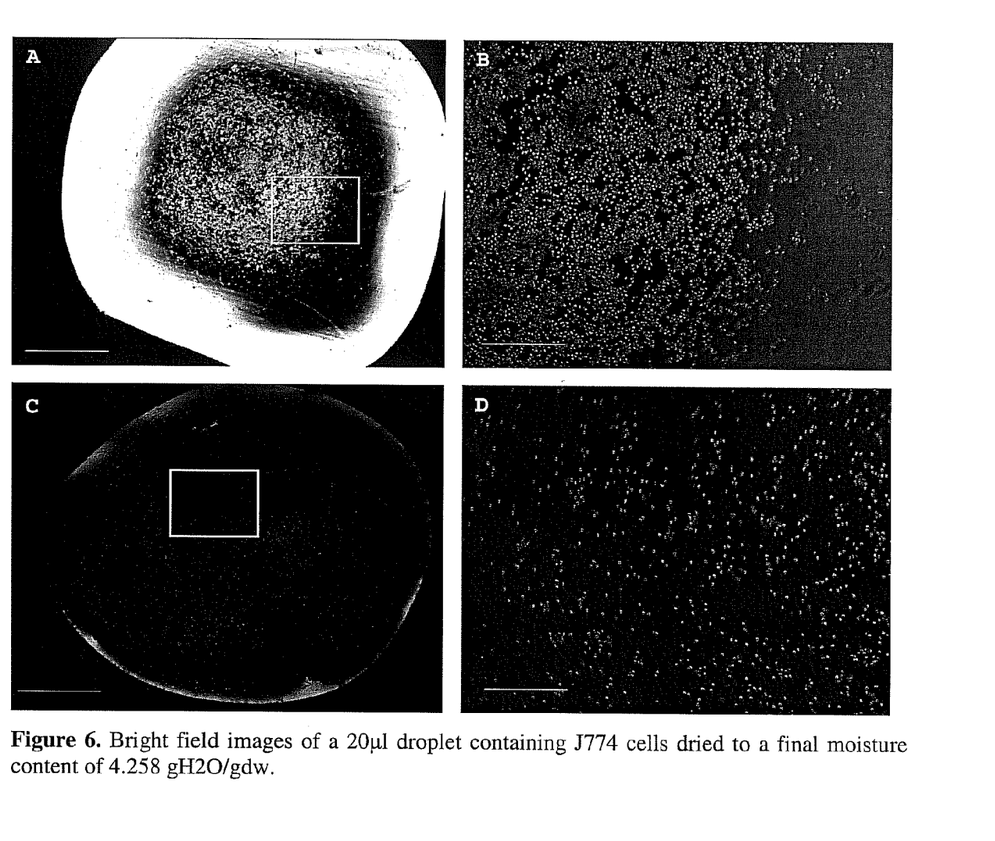
FIG. 6: Bright field images of a 20 μl droplet containing J774 cells dried to a final moisture content of 4.258 gH2O/gdw. Images (A) and (B) were acquired after drying the droplet for 35 minutes in a desiccation chamber. Images (C) and (D) were acquired following drying in a microwave oven for 330 s of accumulative heating time (660 s total process time). The bars in the images (A) and (C) represent a length of 1320 micrometers (μm) and the bars in the images (B) and (D) represent a length of 268 μm.

FIG. 6 shows micrographs of trehalose-loaded cells dried in droplets by both the microwave technique and by processing in a drybox. In both of these cases the samples were dried to the same moisture content based on a bulk gravimetric measurement (4.258 g$H_2$O/gdw). Non-uniformity in cellular distribution was obvious by eye in samples dried in the desiccation chamber. The central region of the droplet, which was clearly wetter than the periphery, contained a white cluster of solids. Microscopy confirmed this as clumped cellular material. Few cells were observed at the periphery. Furthermore a ring of solids could be observed in the periphery, consistent with drying physics that characterize a contact-pinned droplet. This effect was not observed in samples that were dried by microwave. In the microwave processed samples cells are found to be uniformly distributed throughout the sample. Because of the dramatic differences in the distribution of cells in the samples dried by drybox and microwave technique no rigorous quantification technique was used to distinguish the two samples.

Figure 7:
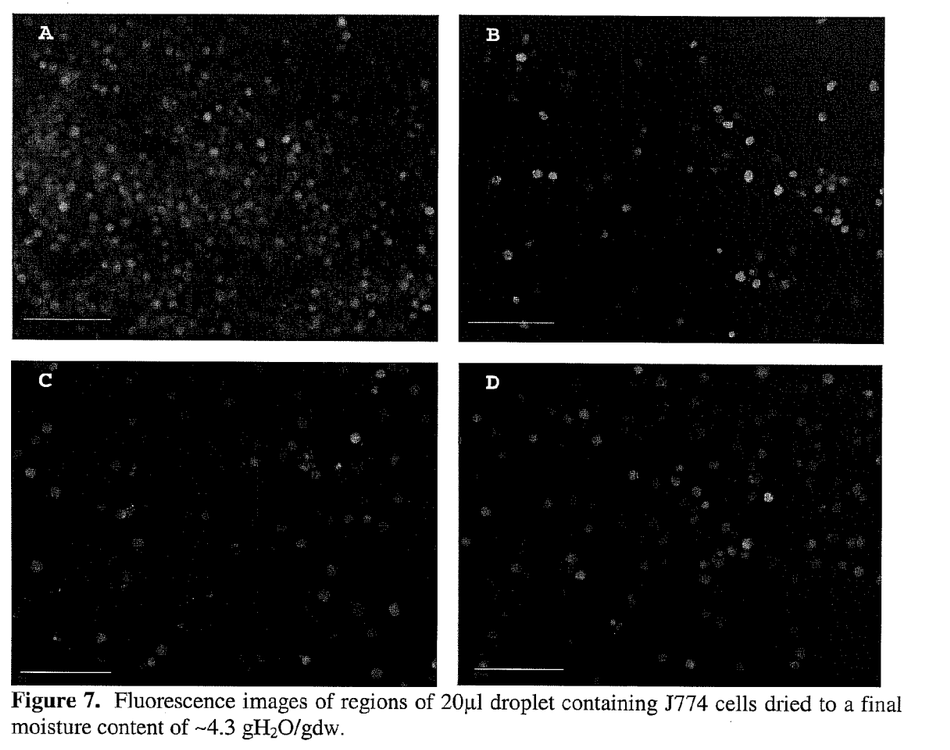
FIG. 7: Fluorescence images of regions of 20 μl droplet containing J774 cells dried to a final moisture content of ~4.3 $gH_2O/gdw$. Image (A) and (B) were acquired after drying the droplet for 35 min in a desiccation chamber (4.258 $gH_2O/gdw$) Images (C) and (D) were acquired following drying with microwave technique for a cumulative 420 s (4.309 gH2O/gdw). Images (A) and (C) are from the central region of the dried droplets and images (B) and (D) are from the edge of the same droplets. The bars in all the images represent a length of 145 μm.

FIG. 7 contains micrographs of samples dried by both techniques, rehydrated, and then stained with Calcein AM/PI solution. The samples were dried to the same moisture content based on a bulk gravimetric measurement (4.258 g$H_2$O/gdw). Consistent with brightfield images, micrograph 7.A clearly show the cluster of cells at the center of a droplet that was dried in a drybox, and the relatively few cells at the edges of the droplet (7B). The clustering of cells precluded a quantitative analysis of viability. As shown in the previous micrographs, the clustering effect is not observed in the case of microwave drying wherein cells are found to be more uniformly distributed throughout the sample. No trend of viability with location was observed in either case.

EXAMPLES

Example 1

Control Cells Dried in Isotonic Trehalose Solution

Cell culture. Mouse macrophage cells were obtained from American Type Culture Collection (Manassas, Va.). Cultures were maintained at 37° C., 10% $CO_2$-90% air in cell culture media consisting of Dulbecco's modified Eagle medium (DMEM) with 4.5 g/L glucose (Mediatech Inc, Herndon, Va.), 10% fetal bovine serum (FBS; Mediatech Inc, Herndon, Va.) and 1% 5000 I.U. Penicillin & 5000 ug/ml Streptomycin solution (Mediatech Inc, Herndon, Va.). Cells were first cultured in 25 cm$^2$ cell culture T-flasks (Corning Incorporated, N.Y.) for 3 days. As cells neared confluence they were detached from the flasks by scraping and then transferred into 50 ml spinner culture flasks (Wheaton Millville, N.J.). An aliquot of cells was taken from an established spinner flask cultures that was maintained at a density of less than 1×10$^6$ cells/ml.

Cell Processing. An aliquot of 5 ml of cell suspension was collected from spinner flask culture and centrifuged at 175×g for 5 min using a Centra CL2 Centrifuge (Thermo Electron Corp., FL). The supernatant was decanted and the cell pellet was resuspended in 11.0 ml of fully complemented Dulbecco's Modified Eagle medium for cell counting in a hemacytometer (Hausser Scientific, Horsham, Pa.), using 0.4% Trypan Blue (Sigma-Aldrich, Mo.) exclusion as an indicator of membrane integrity and viability. Based on this count a cell concentration of 5×10$^5$ viable cells/ml in full complement media was prepared. Cells were plated onto 22 mm square plastic cover slips (Fisher Scientific, Pittsburgh, Pa.) in 20 µl droplets (~10,000 cells/droplet). The cover slips was placed in 35 mm×10 mm tissue culture treated cell culture dishes (Corning Incorporated, N.Y.) and placed inside the incubator for 45 min to allow the cells to attach to the surface of the coverslip.

Cell Drying. Following the incubation period the media was carefully removed by pipette and an equal volume of 200 mM isotonic trehalose-PBS drying solution was placed on top of the plated cells (total osmolality=308 mOsm). This sample was then placed in a single phase 120 volt 2450 MHz Microwave oven for processing (Danby, Ontario, Canada; input specification: 60 Hz AC, 1.05 KW, grounded). Samples were heated in steps, alternating between 30 s active heating steps at full power, and passive cooling steps, wherein the sample was allowed to rest inside the microwave cavity with the door open (30 s). Samples were dried to a final moisture content of 4.258 gH20/gdw.

Cell Survival The viability of microwave-processed cells was evaluated as a function of final moisture content. Immediately after microwave processing the coverslip was removed from the microwave and placed into a P-35 cell culture dish. It was then rehydrated with 100 µl of fully complemented Dulbecco's Modified Eagle medium that had been pre-warmed to 37° C. Samples were then placed in the incubator for 45 minutes to provide time for reattachment to the surface of the coverslip prior to viability assessment. Cell viability was determined using Trypan Blue and Calcein-AM/Propidium Iodide membrane integrity assays (Molecular Probes, Eugene, Oreg.). Following the recovery period in the incubator, the entire 100 µl droplet was gently removed (leaving behind the cells which were attached to the coverslip surface) and collected into a 0.5 ml eppendorf tube. The viability of detached cells in this aliquot was determined by staining with 0.4% Trypan Blue solution and counting in a hemacytometer (Hausser Scientific, Horsham, Pa.). An aliquot of 120 µl of Calcein-AM/Propidium Iodide solution in PBS was added to the attached cells on the coverslip and the sample was then incubated at 37° C. for 5 min. These samples were then imaged using an inverted research microscope (Olympus Biosystems 1×81; Olympus America Inc., Melville, N.Y.) with FITC and PI fluorocubes. The attached cell viability was determined by counting the live (green) and dead (red) cells on three representative images from the same sample. The total viability was estimated using equation 1 (described previously), which takes into consideration the viability of both detached and attached cells. The percentage of cells that were viable after processing to this moisture content was approximately 18%.

Example 2

Trehalose Pre-Treated Cells Dried in Isotonic Trehalose Solution

Cell culture. Same as Example 1

Cell Processing. Mouse macrophage cells were incubated overnight in full complement media containing trehalose at a concentration of 50 mM. Cells were found to load trehalose at a concentration of 160±50 mM (standard error), some of which was expected to be distributed in the cytoplasm. Cells were then dried to a final moisture content of 4.258 gH2O/gdw using the processing method of Example 1.

Cell Drying. Same as Example 1

Cell Survival The method for assessing cell viability was the same as in Example 1. The percentage of cells that were viable after processing to 4.258 gH2O/gdw was approximately 70%.

Cell growth: Long term viability of the microwave processed cells was determined using a metabolic assay based on the reduction of resazurin. The blue and non-fluorescent dye resazurin is reduced to pink and highly fluorescent resorufin by the metabolic activity of living cells. Resazurin was obtained in powdered form (Sigma Aldrich Co., Milwaukee, Wash.). A stock solution of 110 µg/ml was prepared in phosphate-buffered saline (Mediatech Inc, Herndon, Va.), sterile-filtered, and then stored in the dark at 4° C. Microwave processed cell specimens on coverslips were placed inside the wells of a 24-well plate (Corning Incorporated, N.Y.), rehydrated with fully complemented media, and then placed inside the incubator at 37° C. Metabolic function assessment was performed after 4, 8, 18.75, 24, 30, 42, 48, and 54.5 hour recovery periods. One hour prior to the assay point cell cultures were removed from the incubator, the media removed, and 500 µL of phenol red-free fully complemented medium with 10% resazurin solution was added to each well. Following the addition, the plates were incubated for 60 min at 37° C. in the dark. After incubation, the cell viability was assessed in terms of Arbitrary Fluorescence Units (AFU) using a fluorescent plate reader (Synergy HT, Bio-Tek Instruments, Vt.) with a 530 nm excitation and a 590 nm emission filter set. Following each measurement, the resazurin solution was removed from the wells, replaced with 500 ml of full-complement culture medium, and the plates were returned to the incubator. At 48 hours the fraction of viable metabolically active cells in the microwave-treated sample was 64.8%.

Sample Uniformity:

The distribution of the cells within the dried droplets were determined using both brightfield and fluorescence microscopy. Calcein-AM and Propidium Iodide stains were used for fluorescence live-dead staining of the cells as described previously and images were acquired in various regions that spanned the droplet. Representative brightfield images were obtained. By eye, there appeared to be an even distribution of solids throughout the sample. The characteristic ring observed in samples dried by passive techniques was not seen in the microwaved samples. Microscopy revealed an even distribution of cells throughout the sample.

Example 3

Control Cells Dried in Hypertonic Trehalose Solution

Cell Culture. Same as Example 1
Cell Processing. Sample as Example 1
Cell Drying. Same as Example 1 with the following exception:

Following the incubation period the media was carefully removed by pipette and an equal volume of 200 mM hypertonic trehalose-PBS drying solution was placed on top of the plated cells (total osmolality=508 mOsm).

Cell Survival The method for assessing cell viability was the same as in example 1. The percentage of cells that were viable after processing to 4.258 gH2O/gdw was approximately 34%.

Example 4

Trehalose Pre-Treated Cells Dried in Hypertonic Trehalose Solution

Cell culture: Same as Example 1
Cell Processing Sample as Example 2
Cell Drying. Same as Example 3
Cell Survival The method for assessing cell viability was the same as in example 1. The percentage of cells that were viable after processing to 4.258 gH2O/gdw was approximately 54%.

The present invention may be embodied in other forms without departing from the spirit and the essential attributes thereof, and, accordingly, reference should be made to the appended claims, rather than to the forgoing specification, as indicated in the scope of the invention.

We claim:

1. A method for preserving biological material comprising the steps of:
   a. providing a vitrification solution which is at room temperature in the range from 18° C. to 26° C.; said vitrification solution being comprised of: said biological material; a vitrification agent;
   b. microwaving said vitrification solution for a first period of time;
   c. allowing said vitrification solution to rest for a second period of time;
   d. repeating steps b and c until said vitrification solution enters into a glassy state.

2. The method of claim 1 wherein said vitrification agent being water-soluble.

3. The method of claim 2 wherein said vitrification agent being trehalose.

4. The method of claim 1 wherein said biological material being selected from the group comprising: proteins, cells, tissues, organs, cell-based constructs, or combinations thereof.

5. The method of claim 1 wherein said first period of time and said second period of time being equivalent, not equivalent, or a combination thereof.

6. The method of claim 1 wherein said first period of time and said second period of time being in the range from 1 second to 120 seconds.

7. The method of claim 1 wherein the temperature of said vitrification solution does not exceed 50° C. for biological cells and tissues, or above the temperature of thermal denaturation for proteins.

8. The method of claim 1 further comprising the step of: supplying additional desiccation energy from supplemental heat transfer sources.

9. The method of claim 1 wherein said glassy state vitrification solution may be stored above cryogenic temperature.

10. The method of claim 1 wherein said vitrification solution has a glass transition temperature in the range of −150° C. to 30° C.

* * * * *